(12) United States Patent
Wang et al.

(10) Patent No.: US 11,393,257 B2
(45) Date of Patent: Jul. 19, 2022

(54) INFORMATION PROCESSOR, INFORMATION PROCESSING METHOD, PROGRAM, AND WEARABLE DEVICE

(71) Applicant: SONY CORPORATION, Tokyo (JP)

(72) Inventors: QiHong Wang, Tokyo (JP); Masatomo Kurata, Tokyo (JP); Hiroyuki Shigei, Tokyo (JP); Sota Matsuzawa, Tokyo (JP); Naoko Kobayashi, Tokyo (JP); Makoto Sato, Tokyo (JP)

(73) Assignee: SONY CORPORATION, Tokyo (JP)

( * ) Notice: Subject to any disclaimer, the term of this patent is extended or adjusted under 35 U.S.C. 154(b) by 67 days.

(21) Appl. No.: 16/968,404

(22) PCT Filed: Dec. 4, 2018

(86) PCT No.: PCT/JP2018/044586
§ 371 (c)(1),
(2) Date: Aug. 7, 2020

(87) PCT Pub. No.: WO2019/159500
PCT Pub. Date: Aug. 22, 2019

(65) Prior Publication Data
US 2020/0401828 A1    Dec. 24, 2020

(30) Foreign Application Priority Data

Feb. 15, 2018    (JP) .............................. JP2018-024619

(51) Int. Cl.
*G06V 40/60*    (2022.01)
*G06V 40/14*    (2022.01)
(Continued)

(52) U.S. Cl.
CPC .......... *G06V 40/67* (2022.01); *G06V 40/1365* (2022.01); *G06V 40/14* (2022.01); *G06V 40/70* (2022.01)

(58) Field of Classification Search
CPC .......... G06K 9/00912; G06K 9/00087; G06K 9/00892; G06K 2009/00932; H04L 63/08; H04L 9/3231; A61B 5/0245; A61B 5/1172; G04G 21/00; G06F 3/0484; G06F 21/30; G06F 21/32; G06T 1/00; G06T 7/00; H04M 1/67; H04W 12/06; G06V 40/67; G06V 40/1365; G06V 40/14; G06V 40/70

See application file for complete search history.

(56) References Cited

U.S. PATENT DOCUMENTS

2015/0186705 A1*   7/2015   Magi ....................... G06F 1/163
                                                        382/125
2016/0328597 A1   11/2016   Abiko et al.
(Continued)

FOREIGN PATENT DOCUMENTS

EP          2787462 A1      10/2014
JP        2002-312324 A     10/2002
(Continued)

*Primary Examiner* — Abhishek Sarma
(74) *Attorney, Agent, or Firm* — Paratus Law Group, PLLC

(57) ABSTRACT

An information processor including a sensor unit that recognizes an operating tool that comes into contact with a display unit, and a control unit that shows a guidance display for guiding an operation of the operating tool on the display unit.

19 Claims, 12 Drawing Sheets

(51) Int. Cl.
   *G06V 40/70*     (2022.01)
   *G06V 40/12*     (2022.01)

(56) References Cited

U.S. PATENT DOCUMENTS

| | | |
|---|---|---|
| 2017/0024597 A1 | 1/2017 | Cho et al. |
| 2017/0032168 A1 | 2/2017 | Kim |
| 2017/0220838 A1 | 8/2017 | He et al. |
| 2017/0364763 A1 | 12/2017 | Jin et al. |

FOREIGN PATENT DOCUMENTS

| | | |
|---|---|---|
| JP | 2003-091509 A | 3/2003 |
| JP | 2008-217187 A | 9/2008 |
| JP | 2010-130251 A | 6/2010 |
| JP | 2012-070356 A | 4/2012 |
| JP | 2015-018413 A | 1/2015 |
| JP | 2017-182504 A | 10/2017 |

\* cited by examiner

A

B

C

A

B

A

B

INFORMATION PROCESSOR, INFORMATION PROCESSING METHOD, PROGRAM, AND WEARABLE DEVICE

CROSS REFERENCE TO PRIOR APPLICATION

This application is a National Stage Patent Application of PCT International Patent Application No. PCT/JP2018/044586 (filed on Dec. 4, 2018) under 35 U.S.C. § 371, which claims priority to Japanese Patent Application No. 2018-024619 (filed on Feb. 15, 2018), which are all hereby incorporated by reference in their entirety.

TECHNICAL FIELD

The present disclosure relates to an information processor, an information processing method, a program, and a wearable device.

BACKGROUND ART

Conventionally, a technology for authenticating a user of a device has been proposed. For example, Patent Document 1 below describes a wristband type authentication device.

CITATION LIST

Patent Document

Patent Document 1: Japanese Patent Application Laid-Open No. 2002-312324

SUMMARY OF THE INVENTION

Problems to be Solved by the Invention

In such a field, display for performing effective authentication is desired.

An object of the present disclosure is to provide an information processor, an information processing method, a program, and a wearable device that enable display for performing effective authentication.

Solutions to Problem

The present disclosure is, for example,
an information processor including:
a sensor unit that recognizes an operating tool that comes into contact with a display unit; and
a control unit that shows a guidance display for guiding an operation of the operating tool on the display unit.
The present disclosure is, for example,
an information processing method including:
a sensor unit recognizing an operating tool that comes into contact with a display unit; and
a control unit showing a guidance display for guiding an operation of the operating tool on the display unit.
The present disclosure is, for example,
a program that causes a computer to execute an information processing method including:
a sensor unit recognizing an operating tool that comes into contact with a display unit; and
a control unit showing a guidance display for guiding an operation of the operating tool on the display unit.
The present disclosure is, for example,
a wearable device including:
a display unit;
a sensor unit that recognizes an operating tool that comes into contact with the display unit; and
a control unit that shows a guidance display for guiding an operation of the operating tool on the display unit.

Effects of the Invention

According to at least one embodiment of the present disclosure, display for performing effective authentication can be performed. Note that the effects described herein are not necessarily limited, and any of the effects described in the present disclosure may be exerted. Additionally, the contents of the present disclosure should not be interpreted as being limited by the exemplified effects.

MODES FOR CARRYING OUT THE INVENTION

Hereinafter, embodiments and the like of the present disclosure will be described with reference to the drawings. Note that the description will be given in the following order.

<General technology>
<1. First Embodiment>
<2. Second Embodiment>
<3. Third Embodiment>
<4. Fourth Embodiment>
<5. Fifth Embodiment>
<6. Sixth Embodiment>
<7. Modification>

The embodiments and the like described below are preferable specific examples of the present disclosure, and the contents of the present disclosure are not limited to these embodiments and the like.

General Technology

Figure 1:
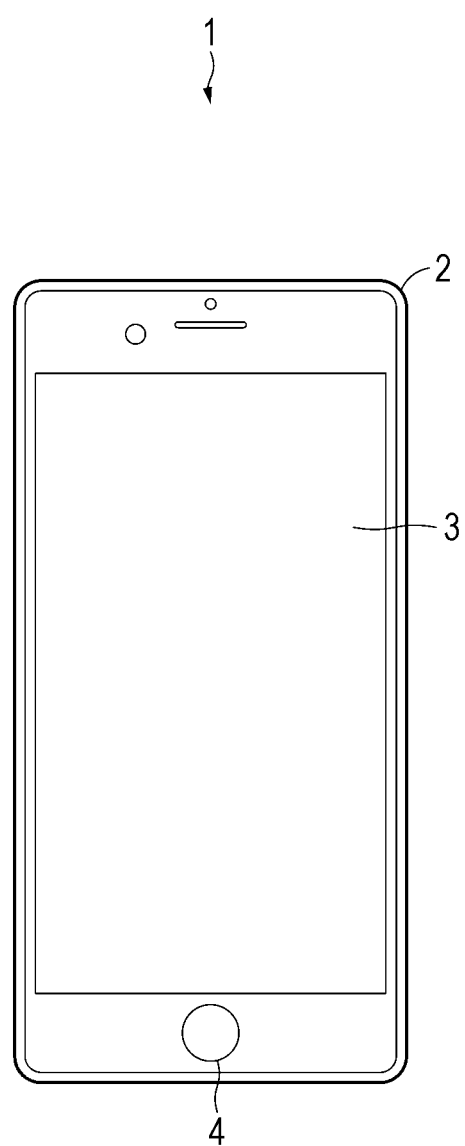
FIG. 1 is a diagram showing an example of the appearance of a general smartphone.

First, a general technology will be described with reference to FIG. 1 to facilitate understanding of the present disclosure. FIG. 1 shows the appearance of a smartphone (smartphone 1), which is an example of a mobile device. The smartphone 1 has, for example, a housing 2, a display 3, and a fingerprint sensor unit 4. The display 3 is provided on one main surface of the housing 2, and the fingerprint sensor unit 4 is provided below the display 3 in the housing 2.

In a case of such a configuration, since the fingerprint sensor unit 4 is provided in an area different from the display 3, the device cannot be designed to be compact as a whole. Additionally, the fingerprint sensor unit 4 applied to the smartphone 1 is often of a capacitance type configured to detect a change in capacitance due to unevenness of a fingerprint. Such a fingerprint sensor unit 4 is susceptible to environmental humidity, and has a problem that it can hardly detect a wet finger in particular.

Additionally, in the general fingerprint authentication system shown in FIG. 1, in a case where a display prompting fingerprint authentication is shown on the display 3, for example, since the position of the display is apart from the position of the fingerprint sensor unit 4, when performing fingerprint authentication, it is necessary to move the finger and the line-of-sight out of the display 3. Hence, there is a problem that an intuitive user interface (UI) cannot be provided. In view of such problems, embodiments of the present disclosure will be described in detail.

1. First Embodiment

[Wristband Type Electronic Device]
(Appearance Example of Wristband Type Electronic Device)

Figure 2:
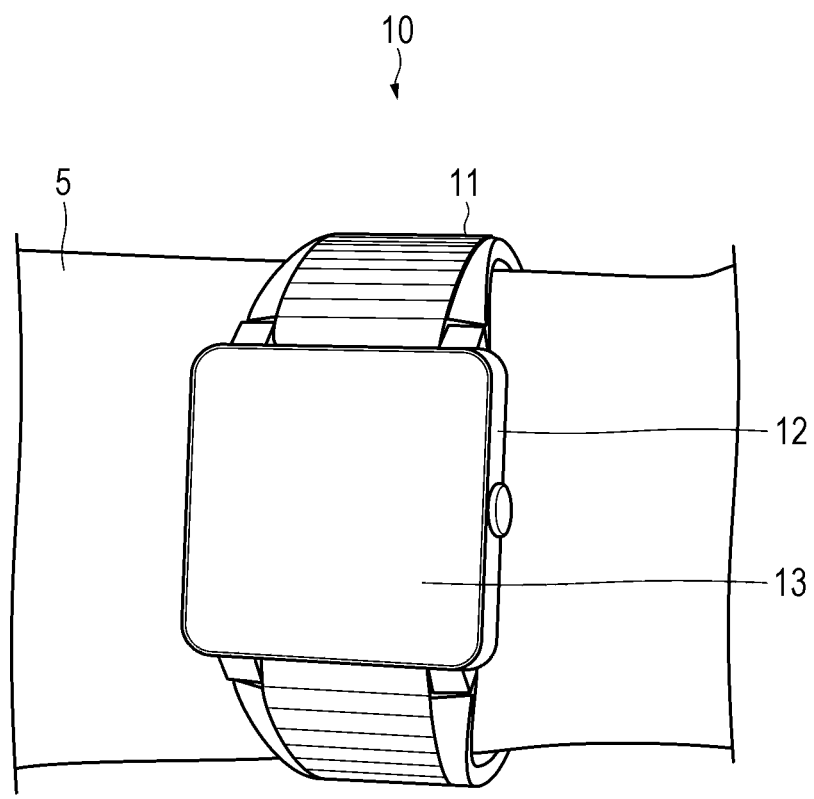
FIG. 2 is a diagram showing an example of the appearance of a wristband type electronic device according to an embodiment.

Next, a first embodiment will be described. The first embodiment is an example in which the present disclosure is applied to an example of an information processor, more specifically, to a wristband type electronic device that is an example of a wearable device. FIG. 2 shows an example of the appearance of a wristband type electronic device (wristband type electronic device 10) according to the first embodiment.

As shown in FIG. 2, the wristband type electronic device 10 is used like a watch, for example. More specifically, the wristband type electronic device 10 has a band portion 11 that is wound around a wrist 5 of the user, and a main body portion 12. The main body portion 12 has a display 13.

(Internal Structure Example of Wristband Type Electronic Device)

Figure 3:
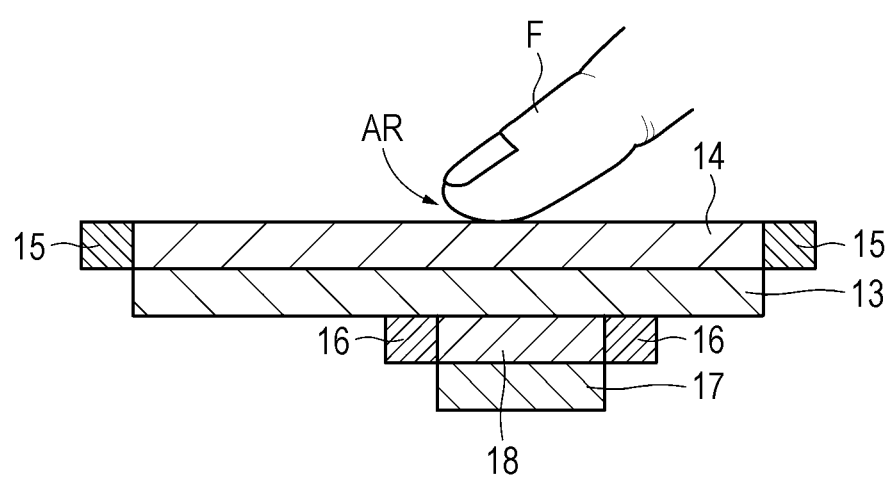
FIG. 3 is a diagram showing an example of the internal structure of the wristband type electronic device according to the embodiment.

FIG. 3 is a partial cross-sectional view for describing an example of the internal structure of the main body portion 12 of the wristband type electronic device 10. The main body portion 12 of the wristband type electronic device 10 has the aforementioned display 13, a light guide plate 14, a light emitting unit 15, a touch sensor unit 16 as an example of a contact detector, an image sensor 17 as an example of a sensor unit, and a lens unit 18, for example.

Generally, as shown in FIG. 3, a contact operation with a fingertip F, which is an example of an operating tool, is performed on the display 13, and presence or absence of contact is detected by the touch sensor unit 16. The main body portion 12 of the wristband type electronic device 10 has a structure in which the light guide plate 14, the display 13, the lens unit 18, and the image sensor 17 are sequentially stacked when viewed from the operation side. Note that contact with the display 13 may include not only direct contact with the display 13, but also indirect contact through another member (e.g., light guide plate 14). Additionally, contact with the display 13 may include not only the fingertip F coming into contact with the display 13, but also the fingertip F approaching the display 13, for example.

Hereinafter, each configuration will be described. The display 13 includes a liquid crystal display (LCD), an organic light emitting diode (OLED), and the like. The light guide plate 14 is a light transmissive member that guides light from the light emitting unit 15 to an area AR where the fingertip F comes into contact, for example. The light guide plate 14 is not limited to a transparent one, and may be any type as long as it transmits light to the extent that an image of a fingerprint of the fingertip F can be captured by the image sensor 17.

The light emitting unit 15 includes a light emitting diode (LED) and the like, and is provided at least partially around the light guide plate 14. Note that the area AR is an area including a position corresponding to the image sensor 17, specifically, an area including at least a position corresponding to a range of imaging by the image sensor 17. The light emitting unit 15 provides light required for imaging by lighting up when capturing an image of a fingerprint, for example.

The touch sensor unit 16 is a sensor that detects contact of the fingertip F with the display 13. As the touch sensor unit 16, a capacitive touch sensor is applied, for example. Other types of touch sensors, such as a resistive film type, may be applied instead. Note that while the touch sensor unit 16 is locally provided near a part below the area AR in FIG. 3, the touch sensor unit 16 may be provided over substantially an entire surface below the display 13.

The image sensor 17 includes a charge coupled device (CCD), a complementary metal oxide semiconductor (CMOS), or the like. The image sensor 17 photoelectrically converts subject light incident through the lens unit 18 into a charge amount to generate an image of the fingerprint of the fingertip F. Various types of processing at the subsequent stage are performed on an image signal obtained through the image sensor 17. The lens unit 18 includes a lens (microlens) provided for each pixel of the image sensor 17.

(Circuit Configuration Example of Wristband Type Electronic Device)

Figure 4:
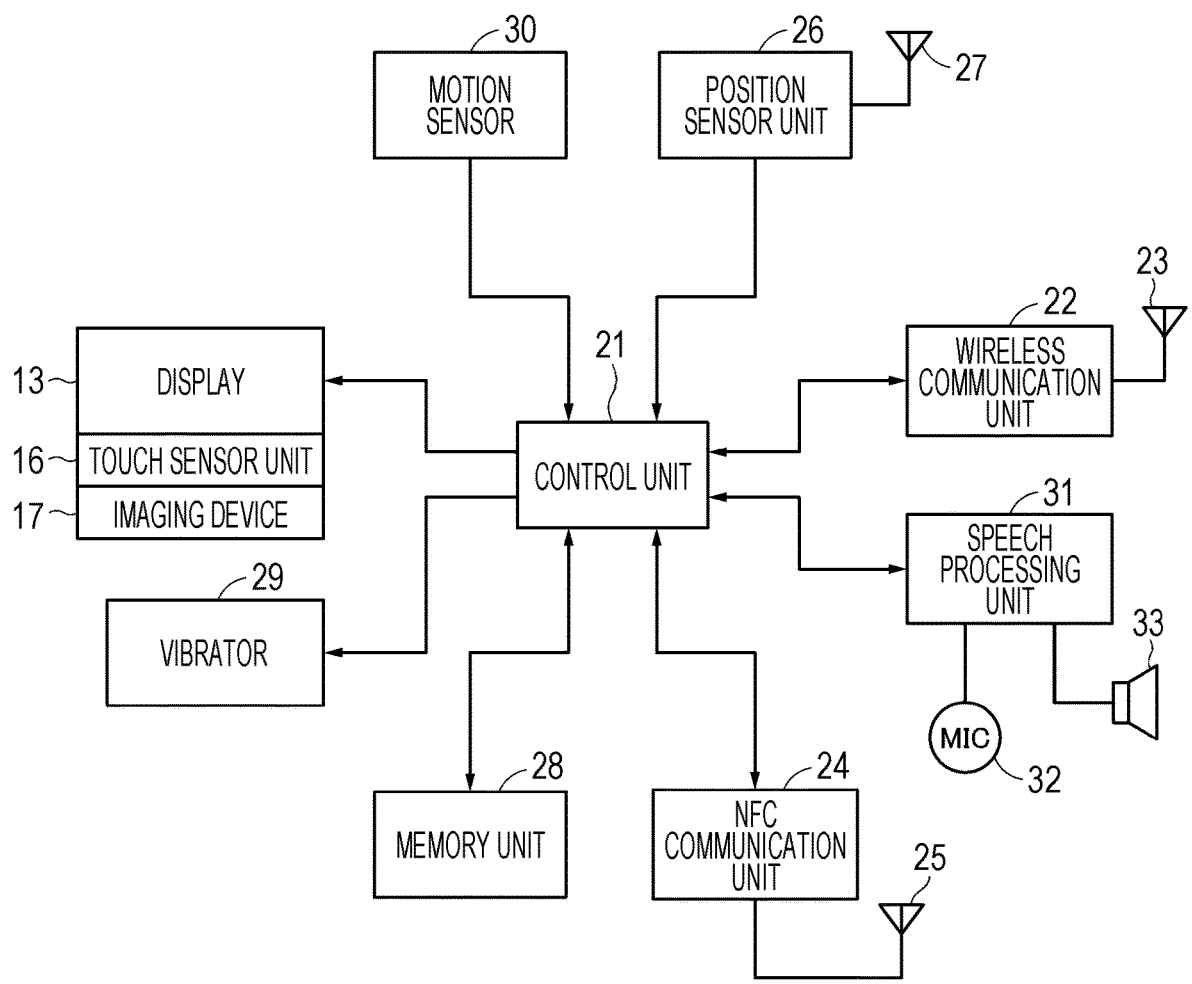
FIG. 4 is a diagram showing an example of the circuit configuration of the wristband type electronic device according to the embodiment.

FIG. 4 is a block diagram showing an example of the circuit configuration and the like of the wristband type electronic device 10. The wristband type electronic device 10 has, in addition to the display 13, the touch sensor unit 16, the image sensor 17, and the like described above, a control unit 21, a wireless communication unit 22, an antenna 23 connected to the wireless communication unit 22, a near field communication (NFC) communication unit 24, an antenna 25 connected to the NFC communication unit 24, a global positioning system (GPS) unit 26, an antenna 27 connected to a position sensor unit 26, a memory unit 28, a vibrator 29, a motion sensor 30, a speech processing unit 31, a microphone 32, and a speaker 33, for example.

The control unit 21 includes a central processing unit (CPU), for example, and controls each unit of the wristband type electronic device 10. As a specific example, the control unit 21 controls information displayed on the display 13, and controls the display 13 to show a guidance display described later. Additionally, the control unit 21 performs various types of image processing on a fingerprint image of the fingertip F captured by the image sensor 17, and performs fingerprint authentication based on an image (fingerprint image) of the fingerprint that is one type of biological information.

The wireless communication unit 22 performs short-range wireless communication with another terminal on the basis of the Bluetooth (registered trademark) standard, for example. The wireless communication unit 22 performs modulation/demodulation processing, error correction processing, and the like in accordance with the Bluetooth (registered trademark) standard, for example.

The NFC communication unit 24 performs wireless communication with a nearby reader/writer on the basis of the NFC standard. Note that although illustration is omitted, power is supplied to each unit of the wristband type electronic device 10 from a battery such as a lithium ion secondary battery. The battery may be wirelessly charged according to the NFC standard.

The position sensor unit 26 is a positioning unit that performs positioning of the current position using a system called global navigation satellite system (GNSS), for example. Data obtained by the wireless communication unit 22, the NFC communication unit 24, and the position sensor unit 26 is supplied to the control unit 21. Then, the control unit 21 executes control based on the supplied data.

The memory unit 28 is a generic term for a read only memory (ROM) in which a program executed by the control unit 21 is stored, a random access memory (RAM) used as a work memory when the control unit 21 executes the program, a nonvolatile memory for data storage, and the like. Note that the memory unit 28 stores the user's fingerprint information for fingerprint authentication. The fingerprint information is initially registered when the wristband type electronic device 10 is used for the first time, for example.

The vibrator 29 is a member that vibrates the main body portion 12 of the wristband type electronic device 10, for example. Vibration of the main body portion 12 by the vibrator 29 notifies the user of an incoming call, reception of an e-mail, and the like.

The motion sensor 30 detects a movement of the user wearing the wristband type electronic device 10. As the motion sensor 30, an acceleration sensor, a gyro sensor, an electronic compass, a barometric pressure sensor, or the like is used. Note that the wristband type electronic device 10 may incorporate a sensor other than the motion sensor 30. For example, a biosensor that detects biological information other than the fingerprint such as blood pressure, pulse, sweat glands (position of sweat glands or degree of sweating from sweat glands), body temperature, or the like of a user wearing the wristband type electronic device 10 may be incorporated. Alternatively, a pressure sensor or the like for detecting whether or not the user has worn the wristband type electronic device 10 may be provided on the back side (side facing the wrist) of the band portion 11 or the main body portion 12.

The microphone 32 and the speaker 33 are connected to the speech processing unit 31, and the speech processing unit 31 performs call processing with a party on the other end connected by wireless communication performed by the wireless communication unit 22. Additionally, the speech processing unit 31 can also perform processing for a speech input operation.

Since the display 13, the touch sensor unit 16, and the like have already been described, overlapping description will be omitted.

[Display Example when Performing Fingerprint Authentication]

Next, display examples when performing fingerprint authentication will be described. Control for showing these display examples on the display 13 is performed by the control unit 21, for example.

Figure 5:
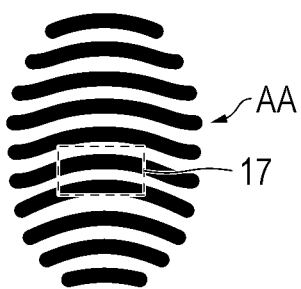
FIG. 5A is a diagram showing an example of display shown at the time of one-touch authentication.
FIG. 5B is a diagram showing an example of display shown at the time of slide authentication.
FIG. 5C is a diagram showing an example of display shown at the time of multi-slide authentication.
Figure 5:
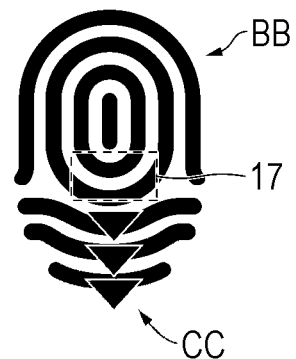
Figure 5:
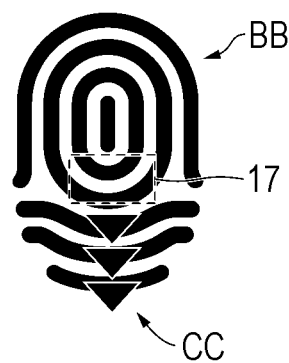
Figure 5:
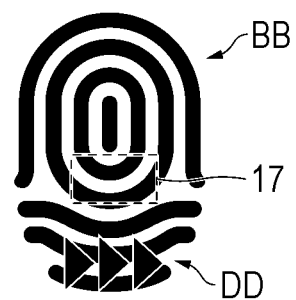
Figure 5:
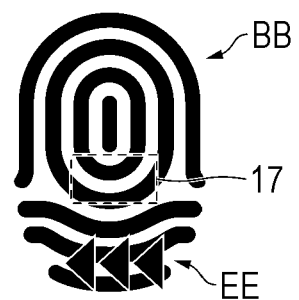

FIG. 5A shows a first example of a display shown when performing fingerprint authentication. As shown in FIG. 5A a display AA imitating a fingerprint is displayed on the display 13, for example. With this display, it is possible to indicate that the position where the display AA is shown is the position where the fingertip F is brought into contact, and it is possible to prompt the user to perform fingerprint authentication. The image sensor 17 is located below at least a part of the position where the display AA is shown. Note that FIG. 5 shows the position of the image sensor 17 for easy understanding.

The user brings the fingertip F into contact with a position corresponding to the display AA. When the contact with the fingertip F is detected by the touch sensor unit 16, the control unit 21 performs control for capturing an image of the fingerprint. According to such control, a fingerprint image, which is information on the fingertip F, is obtained through the image sensor 17. After subjecting the obtained fingerprint image to appropriate image processing, the control unit 21 performs match processing between the fingerprint image and the user's fingerprint image stored in the memory unit 28 to perform authentication. For example, authentication is performed by comparing the degree of coincidence of feature points between fingerprint images. Other known methods can be applied as the authentication method, as a matter of course. Alternatively, authentication based on any biological information or a combination thereof may be performed. Note that the display exemplified in FIG. 5A is an example in which authentication is performed by a single contact, and is not a display accompanied by a guidance display.

With such a configuration, the part where the fingerprint authentication is performed can be integrated with the display. Hence, the wristband type electronic device 10 can be downsized. Additionally, by showing the display for performing fingerprint authentication above the device for performing fingerprint authentication (image sensor 17 in present embodiment), it becomes easy for the user to recognize where to place the fingertip F, and an intuitive UI can be implemented. Additionally, authentication can be performed irrespective of the humidity of the fingertip F, and the accuracy of authentication can be ensured.

FIG. 5B shows a second example of a display shown when performing fingerprint authentication. The second example is an example of a guidance display for guiding the operation of the fingertip F together with the position where the fingertip F is brought into contact. The guidance display in the present embodiment is a display indicating the moving direction of the fingertip F.

For example, as shown in FIG. 5B, as an example of the guidance display, a display CC of three downward-pointing arrows is shown together with a display BB imitating a fingerprint. With this display, it is possible to prompt the user to move the fingertip F downward.

In response to an operation of moving the fingertip F downward, an image of the fingerprint is captured. With this operation, it is possible to obtain more feature points of the fingerprint. By comparing the feature points of the captured fingerprint image with the feature points of the fingerprint image stored in the memory unit 28, more accurate fingerprint authentication can be performed.

FIG. 5C shows a third example of a display shown when performing fingerprint authentication. The display shown on the left side of FIG. 5C is similar to the display shown in FIG. 5B. The display shown in the center of FIG. 5C includes, as an example of the guidance display, a display DD of three rightward-pointing arrows together with the display BB imitating a fingerprint. The display shown on the right side of FIG. 5C includes, as an example of the guidance display, a display EE of three leftward-pointing arrows together with the display BB imitating a fingerprint.

The three displays shown in FIG. 5C are displayed consecutively, for example. For example, based on the display on the left side of FIG. 5C, the fingertip F is slid and an image of the fingerprint is captured. Then, when the touch sensor unit 16 detects that the fingertip F is separated from the display 13, the control unit 21 shows the display shown in the center of FIG. 5C on the display 13. According to the display, the fingertip F is slid rightward and an image of the fingerprint is captured. When the touch sensor unit 16 detects that the fingertip F is separated from the display 13, the control unit 21 shows the display shown on the right side of FIG. 5C on the display 13. According to the display, the fingertip F is slid leftward and an image of the fingerprint is captured.

With such processing, it is possible to obtain more feature points of the fingerprint than feature points of the fingerprint obtained on the basis of the display shown in FIG. 5B, for example. By comparing the feature points of the captured fingerprint image with the feature points of the fingerprint image stored in the memory unit 28, more accurate fingerprint authentication can be performed.

Note that in the following description, authentication performed in response to an operation of bringing the fingertip F into contact with the display 13 once as shown in FIG. 5A is referred to as one-touch authentication as appropriate. Additionally, authentication performed in response to an operation of bringing the fingertip F into contact with the display 13 once and then sliding the fingertip F once as shown in FIG. 5B is referred to as slide authentication as appropriate. Additionally, authentication performed in response to an operation of sliding the fingertip F multiple times on the display 13 as shown in FIG. 5C is referred to as multi-slide authentication as appropriate.

Authentication Processing in First Embodiment (Authentication Processing Flow)

Figure 6:
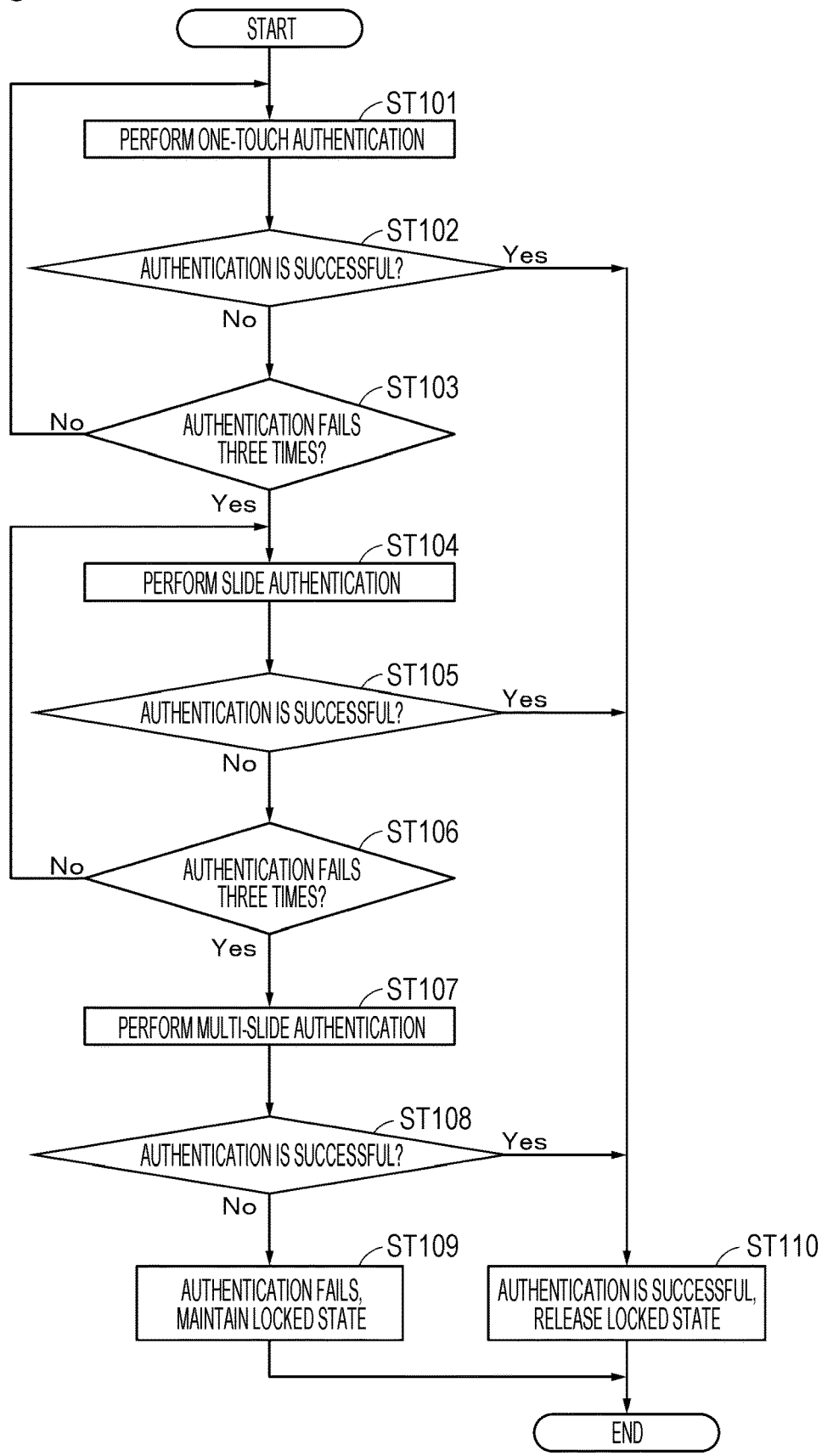
FIG. 6 is a flowchart showing the flow of authentication processing according to a first embodiment.

Next, authentication processing in the first embodiment will be described with reference to a flowchart shown in FIG. 6. The authentication processing in the first embodiment is authentication processing performed when the wristband type electronic device 10 is worn on the wrist 5 and used. Note that the authentication processing described below may be performed after passage of a predetermined time after the wristband type electronic device 10 is worn, or the like.

Before the authentication is successfully performed by the authentication processing, the wristband type electronic device 10 is in a locked state. The locked state may be a state in which use of all the functions of the wristband type electronic device 10 is prohibited, or a state in which use of only a function that does not require authentication (e.g., display of time) is permitted. If the authentication is successful, the locked state is released, and use of all the functions of the wristband type electronic device 10 is permitted. Hereinafter, a specific processing flow will be described. Note that the following processing is performed under the control of the control unit 21 unless otherwise specified.

In step ST101, one-touch authentication is performed. That is, a shape imitating a fingerprint is displayed on the display 13, and when the user brings the fingertip F into contact with the display, fingerprint authentication is performed. Then, the processing proceeds to step ST102.

In step ST102, it is determined whether or not the authentication has been successful. For example, the control unit 21 compares the captured fingerprint image with the fingerprint image stored in the memory unit 28, and if the feature points match by a threshold value or more, determines that the authentication has been successful, and if not, determines that the authentication has failed. If the control unit 21 determines that the authentication has been successful, the processing proceeds to step ST110.

In Step ST110, since the authentication has been successful, the control unit 21 releases the locked state of the wristband type electronic device 10. Thereafter, all the functions of the wristband type electronic device 10 become available.

In the determination processing of step ST102, if the control unit 21 determines that the authentication has failed, the processing proceeds to step ST103. In step ST103, it is determined whether or not the number of authentication failures is equal to or greater than a threshold value (e.g., three times). If the number of authentication failures is less than three, the processing returns to step ST101, and one-touch authentication is performed again. If the number of authentication failures is three or more, the processing proceeds to step ST104.

In step ST104, slide authentication is performed. That is, a shape imitating a fingerprint including a guidance display is displayed on the display 13, and when the user brings the fingertip F into contact with the display and slides the fingertip F once, fingerprint authentication is performed. Here, since the one-touch authentication has failed multiple times, slide authentication is performed to more accurately authenticate the person to be authenticated. Then, the processing proceeds to step ST105.

In step ST105, it is determined whether or not the authentication has been successful. For example, the control unit 21 compares the captured fingerprint image with the fingerprint image stored in the memory unit 28, and if the feature points match by a threshold value or more, determines that the authentication has been successful, and if not, determines that the authentication has failed. If the control unit 21 determines that the authentication has been successful, the processing proceeds to step ST110.

In Step ST110, since the authentication has been successful, the control unit 21 releases the locked state of the wristband type electronic device 10. Thereafter, all the functions of the wristband type electronic device 10 become available.

In the determination processing of step ST105, if the control unit 21 determines that the authentication has failed, the processing proceeds to step ST106. In step ST106, it is determined whether or not the number of authentication failures is equal to or greater than a threshold value (e.g., three times). If the number of authentication failures is less than three, the processing returns to step ST104, and slide authentication is performed again. If the number of authentication failures is three or more, the processing proceeds to step ST107.

In step ST107, multi-slide authentication is performed. That is, a shape imitating a fingerprint including a guidance display is displayed on the display 13, and when the user brings the fingertip F into contact with the display and slides the fingertip F multiple times, fingerprint authentication is performed. Here, since slide authentication has failed multiple times, multi-slide authentication is performed to more accurately authenticate the person to be authenticated. Then, the processing proceeds to step ST108.

In step ST108, it is determined whether or not the authentication has been successful. For example, the control unit 21 compares the captured fingerprint image with the fingerprint image stored in the memory unit 28, and if the feature points match by a threshold value or more, determines that the authentication has been successful, and if not, determines that the authentication has failed. If the control unit 21 determines that the authentication has been successful, the processing proceeds to step ST110.

In Step ST110, since the authentication has been successful, the control unit 21 releases the locked state of the wristband type electronic device 10. Thereafter, all the functions of the wristband type electronic device 10 become available.

In the determination processing of step ST108, if the control unit 21 determines that the authentication has failed, the processing proceeds to step ST109. In step ST109, since the authentication in all of one-touch authentication, slide authentication, and multi-slide authentication has failed, it is determined that the person to be authenticated is not the genuine user of the wristband type electronic device 10. Hence, the control unit 21 maintains the locked state of the wristband type electronic device 10.

(Modification of Authentication Processing)

In the above-described all of authentication processing, one-touch authentication, slide authentication, and multi-slide authentication are performed in accordance with the success or failure of authentication. However, the present invention is not limited to this. For example, the authentication processing may be processing of performing authentication based on slide authentication without first performing one-touch authentication, and performing multi-slide authentication in a case where the authentication based on slide authentication fails multiple times.

2. Second Embodiment

Next, a second embodiment will be described. The second embodiment is generally an example in which different guidance displays are displayed according to security levels. Note that items described in the first embodiment (e.g., appearance, configuration, and the like of wristband type electronic device 10) can be applied to the second embodiment unless otherwise specified. Note that a wristband type electronic device 10 according to the second embodiment has a payment function that enables payment by bringing the wristband type electronic device 10 closer to a reader.

Authentication Processing in Second Embodiment

Figure 7:
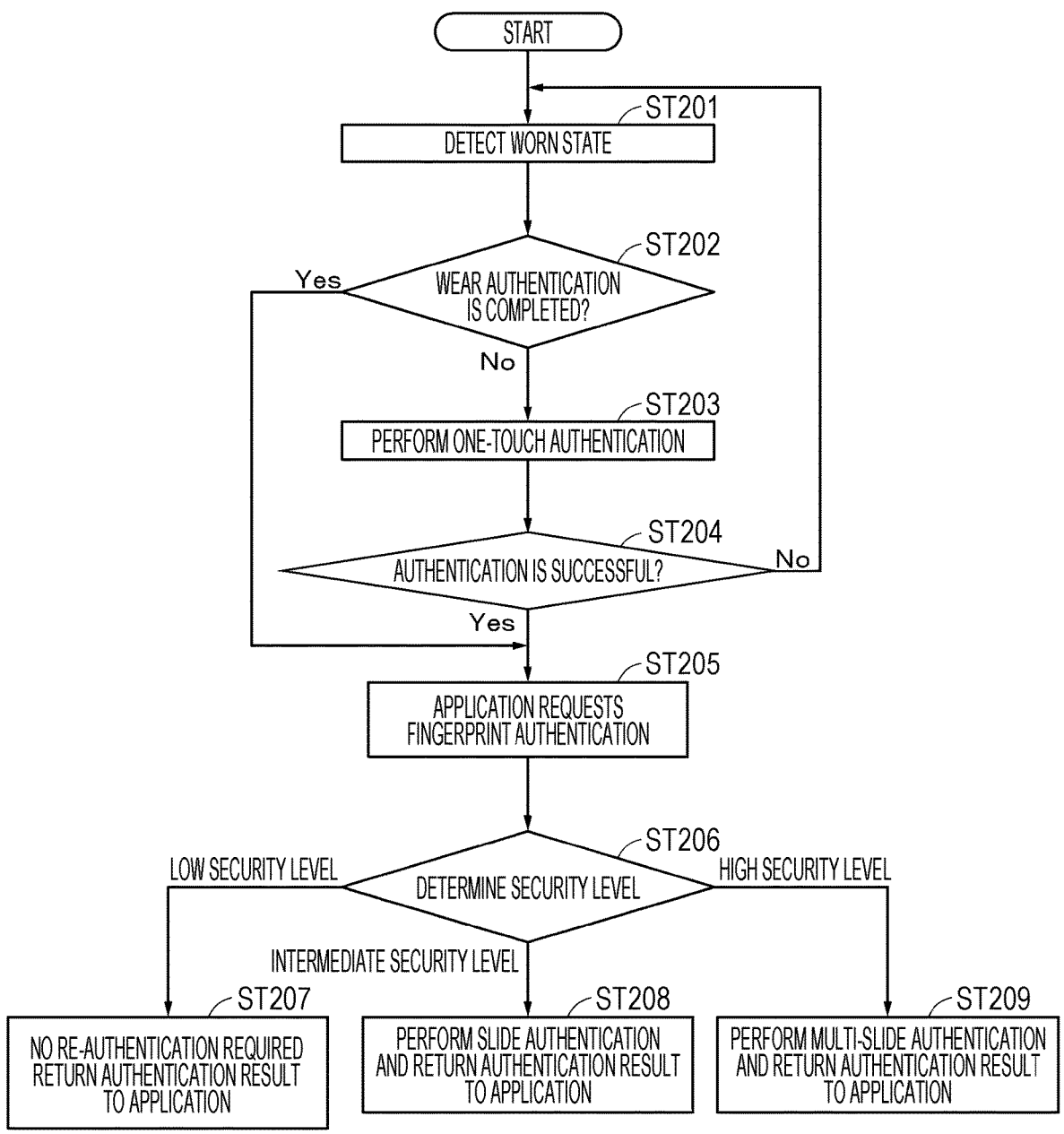
FIG. 7 is a flowchart showing the flow of authentication processing according to a second embodiment.

Authentication processing in the second embodiment will be described with reference to a flowchart shown in FIG. 7. The authentication processing in the second embodiment is generally authentication processing in which processing from step ST201 to step ST204 in the processing shown in FIG. 7 is performed when the wristband type electronic device 10 is worn, and the processing from step ST205 to step ST209 is performed in response to a request from an application that executes a payment function. Note that while the following describes that the authentication processing performed when the wristband type electronic device 10 is worn and the authentication processing performed in response to a request from the application are performed consecutively, the two types of processing do not need to be performed consecutively.

In step ST201, the worn state of the wristband type electronic device 10 is detected. For example, the worn state of the wristband type electronic device 10 is detected on the basis of a detection result by a pressure sensor provided in a band portion 11 of the wristband type electronic device 10. Then, if the wristband type electronic device 10 is worn, the processing proceeds to step ST202.

In step ST202, it is determined whether or not wear authentication, which is authentication performed when the wristband type electronic device 10 is worn, has been completed. For example, a control unit 21 refers to a flag stored in a memory unit 28 and indicating whether or not wear authentication has been completed, and determines whether or not wear authentication has been completed. If wear authentication has not been completed, the processing proceeds to step ST203.

In step ST203, wear authentication is performed by authentication based on one-touch authentication, for example. Then, the processing proceeds to step ST204.

In step ST204, it is determined whether or not the wear authentication has been successful. If the wear authentication has failed, the processing returns to step ST201, and wear authentication according to the worn state is performed. If the wear authentication has been successful, the control unit 21 updates the flag to indicate that the wear authentication has been completed, for example. Then, the processing proceeds to step ST205.

In step ST205, the user makes a payment with so-called electronic money using the wristband type electronic device 10. In step ST205, in order to make such a payment, an application that makes the payment requests the wristband type electronic device 10 to perform fingerprint authentication and send the result of the fingerprint authentication. Then, the processing proceeds to step ST206.

In step ST206, the control unit 21 determines the security level. In the present embodiment, the control unit 21 determines the security level according to the payment amount. For example, if the payment amount is small (e.g., 10,000 yen or less), it is determined that the required security level is "low". Instead, if the payment amount is a predetermined amount (e.g., 10,000 to 100,000 yen or less), it is determined that the required security level is "intermediate". Instead, if the payment amount is large (e.g., more than 100,000 yen), it is determined that the required security level is "high".

If the security level is "low", the processing proceeds to step ST207. In step ST207, since the security level is "low", the control unit 21 determines that only completion of wear authentication is necessary, and re-authentication is not necessary. Here, since wear authentication has already been completed in step ST202, the application returns to the control unit 201 that wear authentication has already been completed and re-authentication is unnecessary. Note that although illustration is omitted, payment using the wristband type electronic device 10 is possible thereafter.

If the result of the determination processing in step ST206 is that the security level is "intermediate", the processing proceeds to step ST208. In step ST208, since the security level is "intermediate", slide authentication that enables more accurate authentication is performed. That is, a display including the guidance display shown in FIG. 5B is shown, for example, and slide authentication is performed. The result of slide authentication is returned to the application. If the result of slide authentication is "success", processing of a function displayed on a display 13 is performed. For example, if the result of slide authentication is "success", payment by the application is performed. Instead, if the result of slide authentication is "failure", the payment by the application is not permitted.

If the result of the determination processing in step ST206 is that the security level is "high", the processing proceeds to step ST209. In step ST209, since the security level is "high", multi-slide authentication that enables more accurate authentication is performed. That is, a display including the guidance display shown in FIG. 5C is shown, for example, and multi-slide authentication is performed. The result of multi-slide authentication is returned to the application. If the result of multi-slide authentication is "success", the payment by the application is performed, and if the result of multi-slide authentication is "failure", the payment by the application is not permitted.

By performing such processing, if wear authentication has been completed, it is permitted to make a purchase at a low price (e.g., tea for about 100 yen), and it is not necessary to perform authentication for every purchase at a low price. Hence, it is possible to achieve both a certain level of security and user convenience. Additionally, when making a purchase at a relatively high price, highly accurate authentication is performed. Hence, payment by impersonation or the like can be prevented.

Modification of Second Embodiment

In a case where the security level is "intermediate", multi-slide authentication may be performed. Then, in a case where the security level is "high", one-touch authentication and multi-slide authentication may be performed. The kind of guidance display to be shown and the way of authentication to be performed according to a security level can be changed as appropriate.

While security levels set assuming face-to-face payment have been described in the above description, the present invention is not limited to this. For example, as shown in Table 1 below, in addition to face-to-face payments, it is also possible to set security levels according to the amount of non-face-to-face payments and functions in Internet banking, and shown guidance displays according to the security levels.

TABLE 1

|  | FACE-TO-FACE PAYMENT | NON-FACE-TO-FACE INTERNET PAYMENT | INTERNET BANKING |
| --- | --- | --- | --- |
| LOW SECURITY LEVEL | 10,000 YEN OR LESS | | |
| INTERMEDIATE SECURITY LEVEL | 10,000 TO 100,000 YEN | 10,000 YEN OR LESS | LOGIN (TO CHECK BALANCE OR OTHER ITEM) |
| HIGH SECURITY LEVEL | 100,000 YEN OR MORE | 10,000 YEN OR MORE | REMITTANCE |

Additionally, the security level may be set in accordance with entry control, data access authority, and the like, as well as payment.

3. Third Embodiment

Next, a third embodiment will be described. The third embodiment is an example in which an operation of a fingertip F is guided by erasing a predetermined display displayed on a display 13 along the moving direction of the fingertip F. Note that the items described in the above embodiment can be applied to the present embodiment unless otherwise specified.

Figure 8:
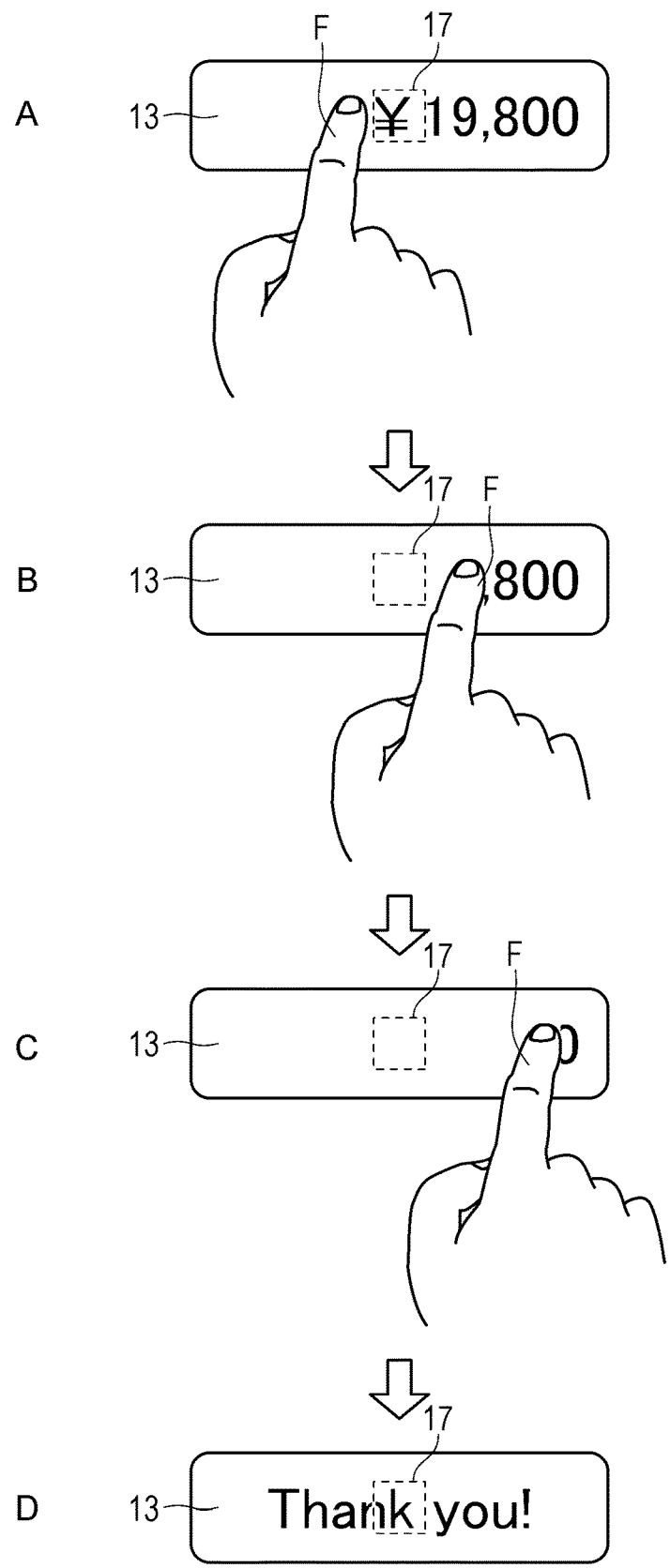
FIG. 8 is a diagram for describing an example of a guidance display according to a third embodiment.

For example, as shown in FIG. 8A, characters (including numbers) "Y19,800" are displayed on the display 13 as an example of a predetermined display. For example, an image sensor 17 is located below the character "Y".

The user first brings the fingertip F into contact with the position of "Y", and then slides the fingertip F along the character string. This operation of the fingertip F is called a swipe. As shown in FIGS. 8B and 8C, the characters disappear along with the sliding operation of the fingertip F. When the fingertip F is slid, the fingertip F passes above the image sensor 17. Hence, a fingerprint image of the fingertip F can be acquired. Slide authentication is performed on the basis of the acquired fingerprint image, and if the fingerprint authentication is established, as shown in FIG. 8D, "Thank you!" is displayed and payment is performed, for example. Note that in a case where the fingerprint authentication fails, the characters "Y19,800" may be displayed again.

By such processing, the user can confirm the amount of payment, and perform an operation of approving the amount of payment by acting as if he/she has actively signed.

Note that the image sensor 17 only needs to be located below at least a part of the path along which the fingertip F slides. Additionally, when displaying the characters "Y19,800" to facilitate understanding of the moving direction of the fingertip F by the user, after sequentially erasing the character string from left to right and erasing all the characters, the characters "Y19,800" may be displayed again. Additionally, this display mode may be repeated. Moreover, when a touch sensor unit 16 detects contact of the fingertip F with the position of "Y", the display density of the adjacent character ("1" in this example) can be reduced, for example. The guidance display that show the characters as if they are fading out allows the user to perceive the direction in which to move the fingertip F. That is, erasing the display may include not only erasing but also changing the density of the display.

4. Fourth Embodiment

Next, a fourth embodiment will be described. Note that the items described in the above embodiment can be applied to the present embodiment unless otherwise specified.

Figure 9:
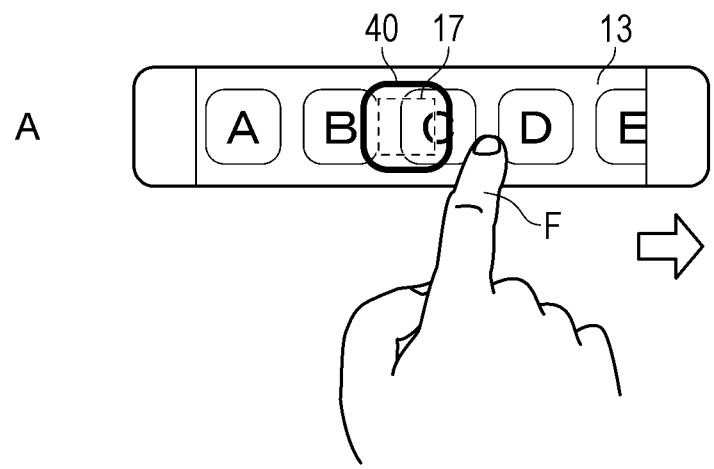
FIG. 9 is a diagram for describing an example of a guidance display according to a fourth embodiment.
Figure 9:
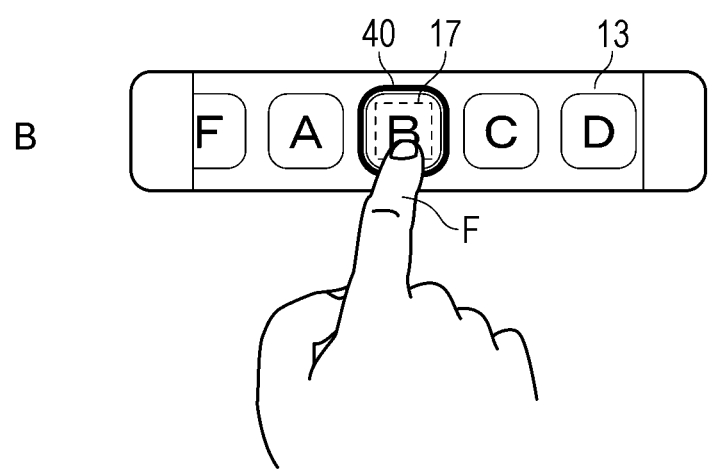

As shown in FIG. 9A, a rectangular frame portion 40 is displayed on the display 13. An image sensor 17 is located below the frame portion 40. Characters A, B . . . , displayed in rectangular frames in FIGS. 9A and 9B indicate icons corresponding to applications. A predetermined icon is displayed in the frame portion 40 in accordance with an operation of sliding a fingertip F of the user. For example, in FIG. 9B, an icon corresponding to application B is displayed in the frame portion 40.

The user performs fingerprint authentication by bringing the fingertip F into contact with the frame portion 40. If the authentication is established, it is possible to log in to the application B. With such processing, it is possible to simultaneously select and log in to the application B. Note that a guidance display such as, for example, an arrow pointing upward or downward may be displayed in the frame portion 40, and the user may be prompted to perform slide authentication or multi-slide authentication in accordance with the display.

5. Fifth Embodiment

Next, a fifth embodiment will be described. Note that the items described in the above embodiment can be applied to the present embodiment unless otherwise specified. The fifth embodiment is generally an example in which a different guidance display is displayed according to a detection result of a motion sensor 30, which is an example of a posture detector.

Figure 10:
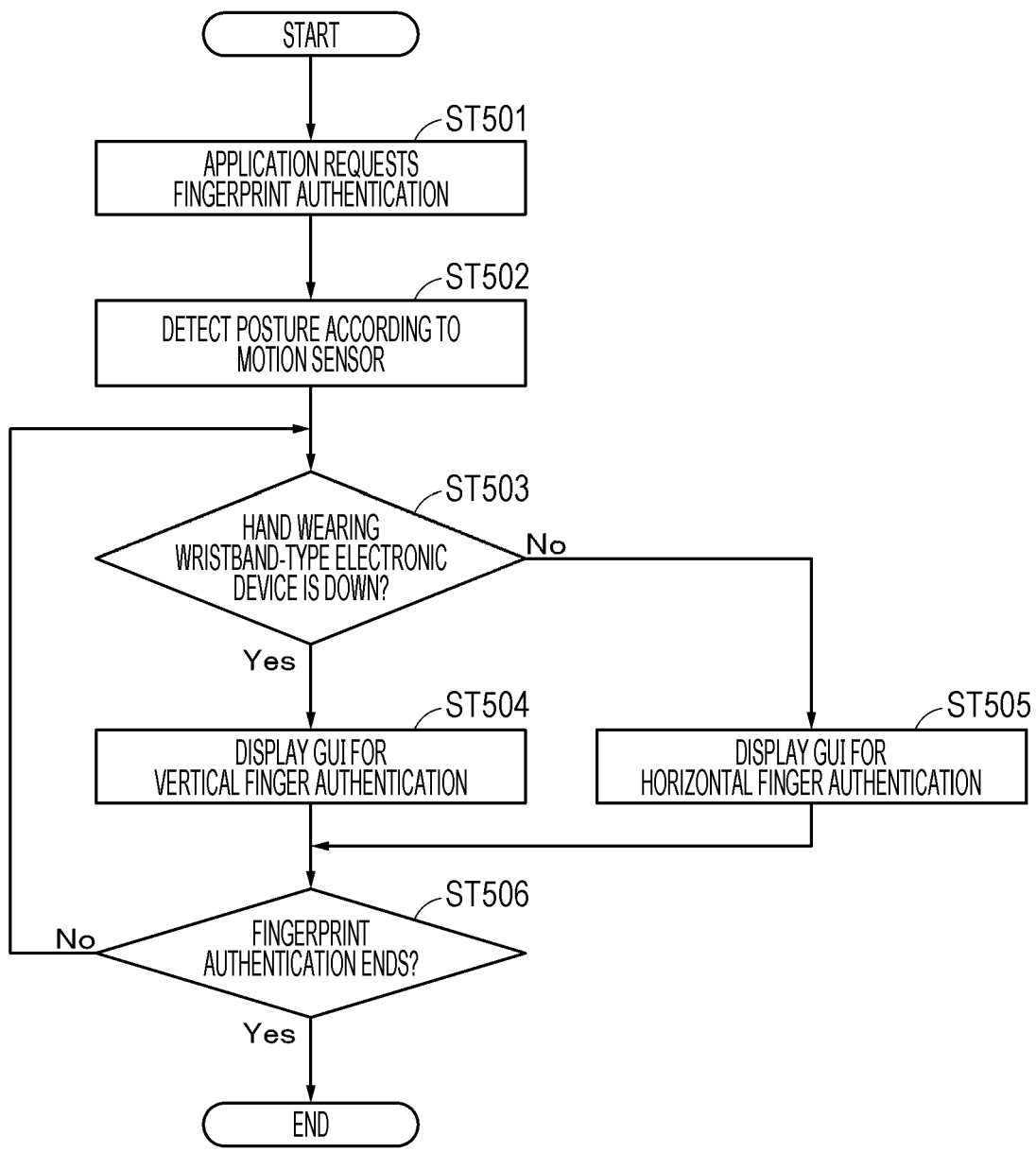
FIG. 10 is a flowchart showing the flow of processing of showing a guidance display according to a fifth embodiment.

FIG. 10 is a flowchart showing the flow of processing in the fifth embodiment. In step ST501, a predetermined application requests fingerprint authentication. Then, the processing proceeds to step ST502.

In step ST502, a control unit 21 detects the posture of a wristband type electronic device 10 on the basis of sensor information supplied from the motion sensor 30. Then, the processing proceeds to step ST503.

In step ST503, the control unit 21 determines from the posture of the wristband type electronic device 10 whether or not the hand wearing the wristband type electronic device 10 is down. If the control unit 21 determines that the hand wearing the wristband type electronic device 10 is down, the processing proceeds to step ST504. In step ST504, the control unit 21 performs control to display a graphical user interface (GUI) for vertical finger authentication on a display 13. Then, the processing proceeds to step ST506.

In the determination processing of step ST503, if the control unit 21 determines that the hand wearing the wristband type electronic device 10 is not down, the processing proceeds to step ST505. In step ST505, the control unit 21 performs control to display a GUI for horizontal finger authentication on the display 13. Then, the processing proceeds to step ST506.

In step ST506, fingerprint authentication using the above-described GUI is performed. Then, it is determined whether or not the fingerprint authentication has been completed. If the fingerprint authentication has been completed, processing according to the authentication result is performed, and then the processing is ended. If the fingerprint authentication has not been completed, the processing returns to step ST503, and the processing after step ST503 is repeated.

Note that in the above-described processing, the case where fingerprint authentication is performed is not limited to a request from an application, and may include other cases (e.g., re-authentication after passage of predetermined time from when wristband type electronic device 10 is worn).

Figure 11:
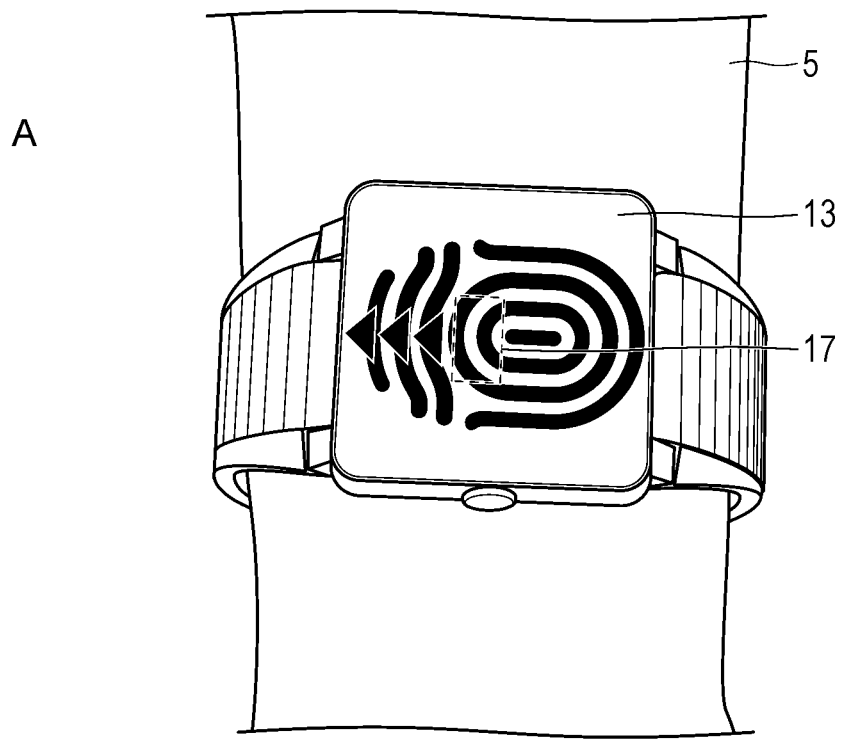
FIG. 11A and FIG. 11B are diagrams for describing examples of a guidance display according to the fifth embodiment.
Figure 11:
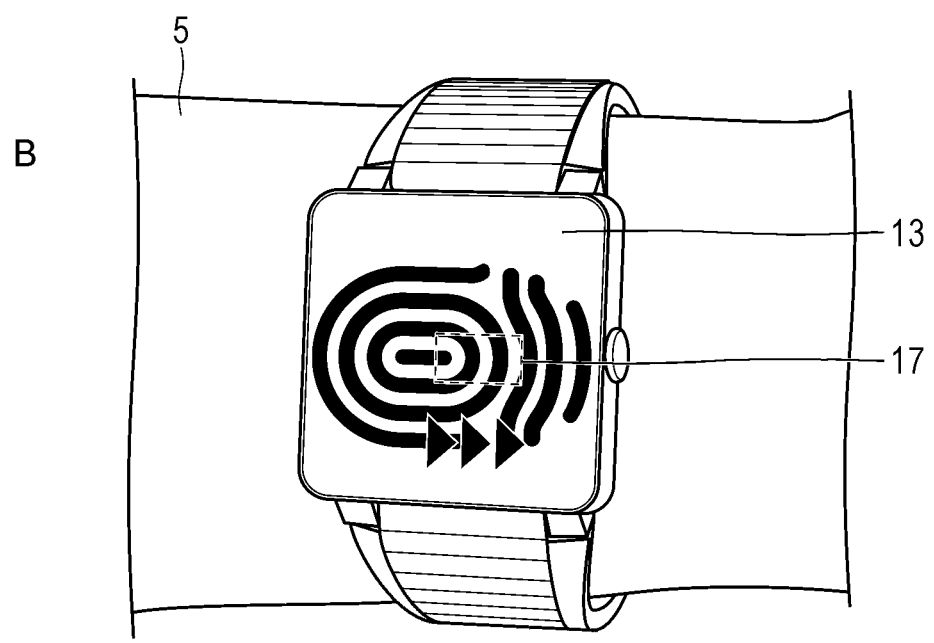

FIG. 11A shows an example of a GUI for vertical finger authentication, and FIG. 11B shows an example of a GUI for horizontal finger authentication.

In the case of the GUI for vertical finger authentication shown in FIG. 11A, a shape imitating a fingerprint is displayed in a direction substantially orthogonal to the extending direction of the user's wrist 5, and a guidance display for guiding the fingertip F to slide in this direction (three arrows in illustrated example) is shown, for example.

In the case of the GUI for horizontal finger authentication shown in FIG. 11B, a shape imitating a fingerprint is displayed in a direction along the extending direction of the user's wrist 5, and a guidance display for guiding the fingertip F to slide in this direction (three arrows in illustrated example) is shown, for example.

As described above, it is also possible to display different guidance displays according to the detection result of the motion sensor 30. By performing such processing, it is possible to display a guidance display with excellent operability even when, for example, the user has his/her arm down while holding a bag, and the like.

6. Sixth Embodiment

Next, a sixth embodiment will be described. Note that the items described in the above embodiment can be applied to the present embodiment unless otherwise specified. The sixth embodiment is generally an example in which guidance display is performed by changing the position of a display shown on a display 13.

Figure 12:
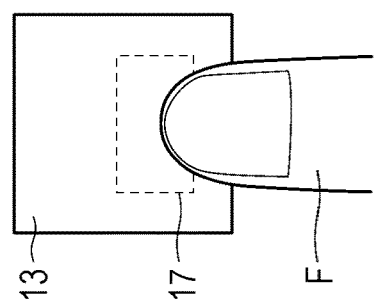
FIG. 12A to FIG. 12E are diagrams for describing an example of a guidance display according to a sixth embodiment.
Figure 12:
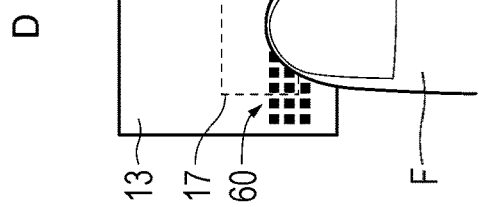
Figure 12:
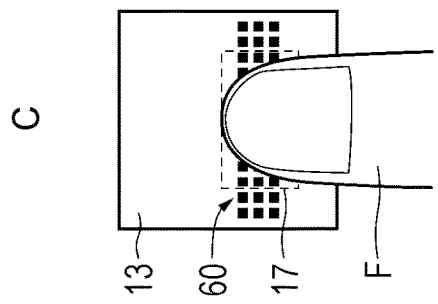
Figure 12:
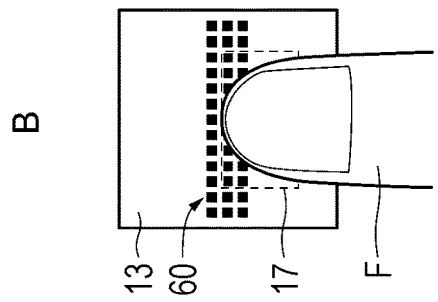
Figure 12:
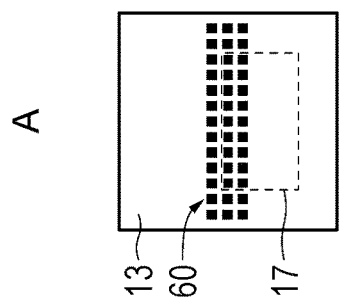

For example, as shown in FIG. 12A, the display 13 shows a linear display 60 including multiple rectangular dots and extending in the horizontal direction. Additionally, an imaging range of an image sensor 17 is indicated by a dotted rectangle. The imaging range overlaps with a position where at least some of the dots included in the display 60 are shown.

As shown in FIG. 12B, the user brings a fingertip F into contact with the position corresponding to the imaging range of the image sensor 17. At this time, to facilitate understanding of the part to bring the fingertip F into contact by the user, the dots at the position overlapping the imaging range of the image sensor 17 may be colored or blinked.

When a touch sensor unit 16 detects the contact of the fingertip F with the display 13, a control unit 21 performs control to change the display of the linear display 60. Specifically, the control unit 21 changes the display position of the dots included in the display 60, thereby controlling the display content to move the display 60 downward as a whole, as shown in FIGS. 12C and 12D. By performing such display processing, it is possible to prompt the user to slide the fingertip F downward. Slide authentication can be performed by the user sliding the fingertip F downward. The control unit 21 may instead control the display content to move the display 60 upward or to the right or left as a whole, as a matter of course.

When the touch sensor unit 16 detects a slide of the fingertip F by a predetermined amount or more, the control unit 21 performs control to erase the display 60 as shown in FIG. 12E, for example. With this operation, the user understands that the operation for fingerprint authentication has been completed, and can take the fingertip F off the display 13.

As described above, it is also possible to perform guidance display by changing the display position shown on the display 13.

Figure 13:
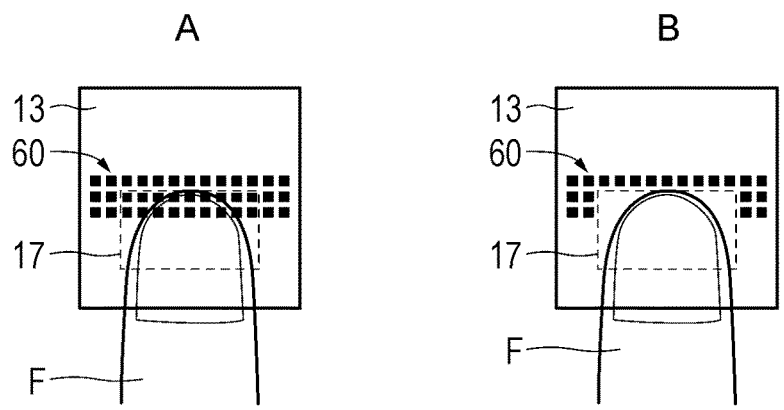
FIG. 13A and FIG. 13B are diagrams for describing processing performed when showing a guidance display according to the sixth embodiment.

Incidentally, as shown in FIG. 13A, if dots are displayed in the imaging range of the image sensor 17 at the time of capturing an image of a fingerprint, the accuracy of fingerprint detection may be affected. For example, in a case where the display 13 includes OLEDs and dots are displayed by light emission of the OLED, mixing of the OLED light when capturing an image of the fingerprint may affect the accuracy of fingerprint detection. Hence, all dots are displayed until the user brings the fingertip F into contact with the display 13. Then, when the touch sensor unit 16 detects that the contact of the fingertip F with the display 13, the dots located within the imaging range may be erased as shown in FIG. 13B.

Alternatively, instead of erasing the dots located within the imaging range, a filter such as a band pass filter (BPF) is inserted in the incident direction of light incident on the image sensor 17. Then, by displaying the dots using light having a wavelength that does not pass through the filter, deterioration in the accuracy of fingerprint authentication due to the display of dots can be prevented.

7. Modification

While multiple embodiments of the present disclosure have been specifically described above, the contents of the present disclosure are not limited to the above-described embodiments, and various modifications based on the technical idea of the present disclosure are possible. Hereinafter, modifications will be described.

Figure 14:
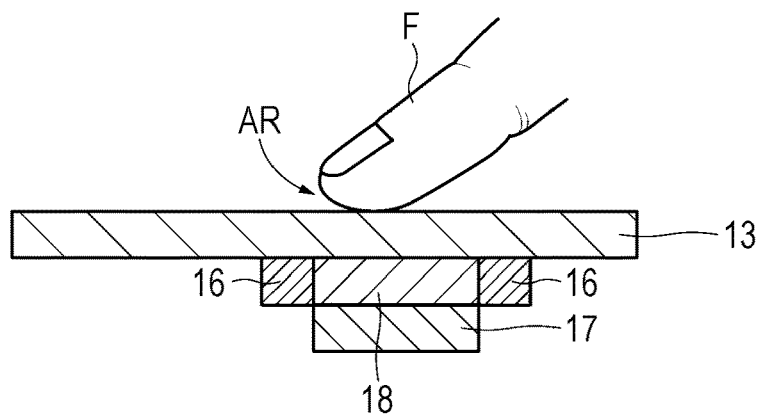
FIG. 14 is a diagram for describing a modification.

The internal structure of the wristband type electronic device 10 described above can be appropriately changed. For example, as shown in FIG. 14, a structure omitting the light guide plate 14 and the light emitting unit 15 may be employed. In this case, a self-luminous display such as an OLED is used as the display 13. Light for imaging may be provided by irradiating the part that comes into contact with the fingertip F with light from the display 13. With this configuration, the light guide plate 14 becomes unnecessary, and the thickness of the device can be reduced. Additionally, the touch sensor unit 16 may be provided on the other main surface side (e.g., upper surface side) of the display 13 in the embodiment.

Figure 15:
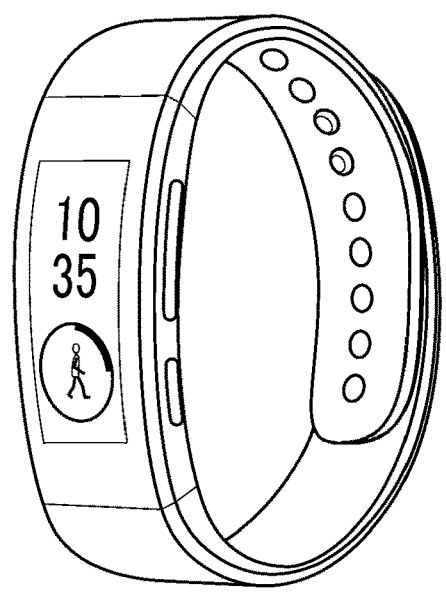
FIG. 15 is a diagram for describing a modification.

The shape and the like of the wristband type electronic device 10 can also be appropriately changed. For example, as shown in FIG. 15, a device in which the band portion 11 and the main body portion 12 are integrally formed may be used. Additionally, the wearable device is not limited to a wristband type electronic device, but may be a smartphone or a portable audio player. Additionally, the present disclosure can be applied to electronic devices such as a personal computer and robot devices. Additionally, the present disclosure can be applied to authentication performed when using an on-vehicle device and authentication performed by an automatic teller machine (ATM) in a bank.

The above-described wristband type electronic device 10 may have a function of notifying the other party using fingerprint authentication of a message. For example, multiple messages are displayed on the display 13. When the user slides a predetermined message from among the multiple messages, the authentication described in the embodiment is performed. When the authentication is established, the other party is notified of the message through the wireless communication unit 22. As the message, a message to a family member such as "I'm coming home" can be set, for example. The message may be a message to a boss, a friend, or the like, and the content of the message can be set as appropriate.

In the above-described finger authentication for sending a message, the destination of the message may be specified in accordance with the type of the authenticated finger (thumb, forefinger . . . , little finger). For example, the user sets the association between the type of finger and the destination, such as father for thumb, mother for forefinger, and sister for little finger. Then, when the user wants to send a message "I'm coming home" to the mother, the user slides the forefinger with the message. If the authentication is established, the mother is notified of the message "I'm coming home". Even in such a case, guidance display can be performed. For example, multiple messages may be shown on the display, or a message to return home may be automatically displayed at a certain time (e.g., in the evening). Multiple destinations may be displayed on the left side of the display, and authentication may be performed when a predetermined destination is touched with a finger. Then, if the authentication is established, multiple messages may be displayed on the right side of the display as a guidance display. The finger contacting the display to specify the destination may then be guided to directly slide to the desired message.

While the above-described embodiments use a fingertip of a person as an example of an operating tool, the present invention is not limited to this. For example, the operating tool may be a pen-shaped device. Then, authentication may be performed by recognizing a specific shape formed at the pen tip.

While the embodiments described above use the moving direction of the fingertip F as an example of the operation of the operating tool (fingertip F) to be guided, the present invention is not limited this. For example, the number of times of contact with the fingertip F or the type of finger (thumb, index finger, or another finger) may be used, or a combination of these may be used. Then, a guidance display indicating the number of times of contact or the type of finger may be displayed. For example, as the required security level increases, the number of times of contact with the fingertip F may be guided to increase, so that the authentication may be performed multiple times by multiple contacts of the fingertip F.

In the above-described embodiments, guidance of the operating tool by voice or the like may be performed. Note, however, that when the user brings the fingertip F into contact, the user's line-of-sight is focused on the contact point. Hence, a configuration in which the user can recognize the guidance of the operating tool with the same perception (vision) is preferable.

multiple image sensors 17 may be provided, and multiple positions where fingerprint authentication can be performed may be provided on the display 13.

The present disclosure can also be implemented by an apparatus, a method, a program, a system, and the like. For example, a program that performs the function described in the above-described embodiment can be provided in a downloadable state, and a device that does not have the function described in the embodiment can download and install the program to control the device in the manner described in the embodiment. The present disclosure can also be implemented by a server that distributes such a program. Additionally, the items described in each of the embodiments and modifications can be appropriately combined.

The present disclosure can also adopt the following configurations.

(1)
An information processor including:
a sensor unit that recognizes an operating tool that comes into contact with a display unit; and
a control unit that shows a guidance display for guiding an operation of the operating tool on the display unit.

(2)
The information processor according to (1), in which
the control unit performs authentication on the basis of biological information on the operating tool obtained by the sensor unit.

(3)
The information processor according to (2), in which
the biological information is authentication based on at least a fingerprint, a sweat gland, a pulse, a blood pressure, a body temperature, or a combination thereof.

(4)
The information processor according to (2), in which
the control unit performs processing of a function displayed on the display unit on the basis of authentication based on the biological information.

(5)
The information processor according to any one of (1) to (4), in which
the guidance display is a display indicating at least one of a moving direction of the operating tool, the number of times of contact of the operating tool, or a type of the operating tool.

(6)
The information processor according to any one of (1) to (5), in which
the control unit shows a different guidance display on the display unit according to a security level.

(7)
The information processor according to any one of (1) to (5), in which
the control unit guides an operation of the operating tool by erasing, along a moving direction of the operating tool, a predetermined display shown on the display unit.

(8)
The information processor according to any one of (1) to (5), in which
the control unit shows the guidance display at a position corresponding to the sensor unit on the display unit.

(9)
The information processor according to any one of (1) to (5) further including a posture detector, in which
the control unit shows a different guidance display according to a detection result by the posture detector.

(10)
The information processor according to any one of (1) to (5), in which
the control unit performs the guidance display by changing a position of a display shown on the display unit.

(11)
The information processor according to any one of (1) to (10), in which
the control unit shows, on the display unit, a display that does not include the guidance display and indicates a contact position of the operating tool.

(12)
The information processor according to any one of (1) to (11), in which
the information processor has a structure in which the display unit, the sensor unit, and a contact detector that detects contact of the operating tool with the display unit are stacked on top of one another.

(13)
The information processor according to (12) further including:
a light emitting unit; and
a light guiding unit that guides light from the light emitting unit to a position where the operating tool comes into contact with the display unit.

(14)
The information processor according to (12), in which
the display unit is a self-luminous display, and has a configuration in which a position where the operating tool comes into contact with the display unit is irradiated with light from the display unit.

(15)
The information processor according to (14), in which
the control unit erases a display shown at a position corresponding to the sensor unit when contact of the operating tool is detected by the contact detector.

(16)
The information processor according to any one of (1) to (15), in which
the operating tool is a fingertip, and the sensor unit is an image sensor.

(17)
An information processing method including:
a sensor unit recognizing an operating tool that comes into contact with a display unit; and
a control unit showing a guidance display for guiding an operation of the operating tool on the display unit.

(18)
A program that causes a computer to execute an information processing method including
a sensor unit recognizing an operating tool that comes into contact with a display unit, and
a control unit showing a guidance display for guiding an operation of the operating tool on the display unit.

(19)
A wearable device including:
a display unit;
a sensor unit that recognizes an operating tool that comes into contact with the display unit; and
a control unit that shows a guidance display for guiding an operation of the operating tool on the display unit.

REFERENCE SIGNS LIST

10 Wristband type electronic device
13 Display
14 Light guide plate
Light emitting unit
16 Touch sensor unit
17 Image sensor
21 Control unit
30 Motion sensor

The invention claimed is:

1. An information processor comprising:
a sensor unit configured to
recognize an operating tool that comes into contact with a display unit, and
obtain biological information related to a user of the operating tool; and
a control unit configured to
perform authentication based on the obtained biological information, and
initiate display of a guidance display for guiding an operation of the operating tool on the display unit,
wherein the guidance display is determined according to a result of the authentication performed based on the obtained biological information, and
wherein the control unit is implemented via at least one processor.

2. The information processor according to claim 1,
wherein the control unit is further configured to perform the authentication based on biological information on the operating tool obtained by the sensor unit.

3. The information processor according to claim 2,
wherein the obtained biological information includes at least one of a fingerprint, a sweat gland, a pulse, a blood pressure, or a body temperature.

4. The information processor according to claim 2,
wherein the control unit is further configured to perform processing of a function displayed on the display unit based on the authentication performed based on the obtained biological information.

5. The information processor according to claim 1,
wherein the guidance display indicates at least one of a moving direction of the operating tool, a number of times of contact of the operating tool, or a type of the operating tool.

6. The information processor according to claim 1,
wherein the control unit initiates display of a different guidance display on the display unit according to a security level.

7. The information processor according to claim 1,
wherein the control unit initiates display of the guidance display for guiding the operation of the operating tool by erasing, along a moving direction of the operating tool, a predetermined display shown on the display unit.

8. The information processor according to claim 1,
wherein the control unit initiates display of the guidance display at a position corresponding to the sensor unit on the display unit.

9. The information processor according to claim 1 further comprising:
a posture detector,
wherein the control unit initiates display of a different guidance display according to a detection result by the posture detector.

10. The information processor according to claim 1,
wherein the control unit initiates display of the guidance display by changing a position of a display shown on the display unit.

11. The information processor according to claim 1,
wherein the control unit is further configured to initiate display, on the display unit, of a display that does not include the guidance display and indicates a contact position of the operating tool.

12. The information processor according to claim 1,
wherein the information processor has a structure in which the display unit, the sensor unit, and a contact detector configured to detect contact of the operating tool with the display unit are stacked on top of one another.

13. The information processor according to claim 12, further comprising:
a light emitting unit; and
a light guiding unit configured to guide light from the light emitting unit to a position where the operating tool comes into contact with the display unit.

14. The information processor according to claim 12,
wherein the display unit is a self-luminous display, and
wherein the display unit has a configuration in which a position where the operating tool comes into contact with the display unit is irradiated with light from the display unit.

15. The information processor according to claim 14,
wherein the control unit is further configured to initiate erasure of a display shown at a position corresponding to the sensor unit when contact of the operating tool is detected by the contact detector.

16. The information processor according to claim 1,
wherein the operating tool includes a fingertip, and
wherein the sensor unit is an image sensor.

17. An information processing method comprising:
recognizing, by a sensor unit, an operating tool that comes into contact with a display unit;
obtaining biological information related to a user of the operating tool;
performing authentication based on the obtained biological information; and
displaying a guidance display for guiding an operation of the operating tool on the display unit,
wherein the guidance display is determined according to a result of the authentication performed based on the obtained biological information.

18. A non-transitory computer-readable storage medium having embodied thereon a program, which when executed by a computer causes the computer to execute an information processing method, the method comprising:
recognizing an operating tool that comes into contact with a display unit;
obtaining biological information related to a user of the operating tool;
performing authentication based on the obtained biological information; and
displaying a guidance display for guiding an operation of the operating tool on the display unit,
wherein the guidance display is determined according to a result of the authentication performed based on the obtained biological information.

19. A wearable device comprising:
a display unit;
a sensor unit configured to
recognize an operating tool that comes into contact with the display unit, and
obtain biological information related to a user of the operating tool; and
a control unit configured to
perform authentication based on the obtained biological information, and
initiate display of a guidance display for guiding an operation of the operating tool on the display unit,
wherein the guidance display is determined according to a result of the authentication performed based on the obtained biological information, and wherein the control unit is implemented via at least one processor.

\* \* \* \* \*